United States Patent [19]
Ashbrook

[11] Patent Number: 5,435,913
[45] Date of Patent: Jul. 25, 1995

[54] FLUID TREATING APPARATUS

[76] Inventor: Clifford L. Ashbrook, R.R. 2, Box 439, Spicewood, Tex. 78669

[21] Appl. No.: 227,501

[22] Filed: Apr. 14, 1994

[51] Int. Cl.$^6$ ............................................. C02F 1/20
[52] U.S. Cl. .................................. 210/188; 95/260; 210/199; 210/205; 210/512.1; 366/165.5; 366/162.4; 366/173.2
[58] Field of Search ............... 95/260, 261; 210/738, 210/764, 787, 788, 188, 198.1, 199, 205, 512.1, 512.2; 366/165, 173

[56] References Cited

U.S. PATENT DOCUMENTS

| | | | |
|---|---|---|---|
| 2,773,029 | 12/1956 | Sebald | 210/16 |
| 3,288,292 | 11/1966 | Stone | 210/97 |
| 3,533,506 | 10/1970 | Carr | 210/84 |
| 3,539,009 | 11/1970 | Kudlaty | 210/90 |
| 4,261,521 | 4/1981 | Ashbrook | 241/5 |
| 4,645,606 | 2/1987 | Ashbrook et al. | 210/695 |
| 4,726,686 | 2/1988 | Wolf et al. | 366/165 |
| 4,764,283 | 8/1988 | Ashbrook et al. | 210/695 |
| 4,883,603 | 11/1989 | Roggestein et al. | 210/802 |
| 4,957,626 | 9/1990 | Ashbrook et al. | 210/695 |
| 5,082,633 | 1/1992 | Stuper | 422/133 |
| 5,114,576 | 5/1992 | Ditzler et al. | 210/195 |
| 5,116,519 | 5/1992 | Michaluk | 210/788 |
| 5,171,090 | 12/1992 | Wiemers | 366/165 |
| 5,318,702 | 6/1994 | Ashbrook | 210/188 |

*Primary Examiner*—Peter A. Hruskoci
*Attorney, Agent, or Firm*—Donald R. Comuzzi; Christopher L. Makay

[57] ABSTRACT

An apparatus for treating fluids by increasing the fluid's rate of diffusion, removing minerals in solution, releasing entrained gases, and destroying bacteria includes a pair of cascaded vortex nozzles positioned in opposed relation. Each of the vortex nozzles communicates with a fluid source to receive a fluid stream which it rotates. The cascaded vortex nozzles feed their rotating fluid stream into the rear of the vortex nozzle with which they are cascaded. The rotating fluid streams fed into the vortex nozzles combine with the rotating fluid stream within each nozzle. The combined streams then circularly rotate and exit the opposed vortex nozzles to collide in a chamber. The collision between the combined rotating streams results in the breaking of the bonds holding the fluid, gases, and minerals in their molecular array, thus, increasing the fluid's diffusion rate, allowing the gases to escape, the minerals to agglomerate, and destroying bacteria. By cascading the vortex nozzles to combine the streams, the compression waves, shearing effect, and velocity of the streams at the impingement point within the chamber between the opposed nozzles are all greatly enhanced to produce a higher diffusion rate, greater removal of gases, agglomeration of minerals in solution, and the destruction of bacteria.

6 Claims, 2 Drawing Sheets

FLUID TREATING APPARATUS

BACKGROUND OF THE INVENTION

1. Field of the Invention

The present invention relates to an apparatus for treating water and other liquids by shattering their molecular arrays to remove minerals in solution and entrained gases. The shattering of the molecular arrays of the water or other liquids allows the gases to escape into the atmosphere while agglomerating the solids for easier removal through settling and/or filtration. Furthermore, the reduction of the molecular arrays into free molecules or small clusters of molecules increases the ability of the water or other liquids to diffuse through permeable solids which, in turn, increases the pressure exerted against a permeable solid as the water or other liquid passes through it. Additionally, the present invention kills bacteria in the water or other liquids through compression which ruptures their cell structure.

2. Description of the Related Art

Certain characteristics of water and other liquids containing entrained gases (e.g. $CO_2$ and/or $N_2$) and dissolved minerals (e.g. Ca and/or Fe) have been discussed in my U.S. Pat. No. 4,261,521. Further testing has revealed new information and uses for the basic apparatus disclosed therein. Although the apparatus of U.S. Pat. No. 4,261,521, may be used to alter the molecular array of any fluid to disentrain gases and agglomerate solids, the fluid described will be water for ease of disclosure and to aid in the understanding of the invention.

The molecular structure of water in liquid form is typically a tetrahedron made up of five individual $H_2O$ molecules bonded together such that one $H_2O$ molecule is positioned at each leg of the tetrahedron with a fifth positioned at its center. The individual $H_2O$ molecules aggregate into a tetrahedron because of an affinity for one another due to their hydrogen bonds. Furthermore, the tetrahedrons of $H_2O$ molecules have a similar affinity and, thus, also aggregate. Accordingly, when water remains relatively quiescent, the tetrahedrons of $H_2O$ molecules associate to form a plurality of large arrays of bound $H_2O$ molecules. As the arrays of tetrahedrons increase in size, the ability of the water to diffuse through permeable solids decreases because many of the large arrays of bound $H_2O$ molecules do not readily pass through the permeable solids.

Additionally, with the above-described molecular configuration, impurities enter the liquid water in the form of entrained gases and dissolved elemental minerals. That is, in addition to the individual $H_2O$ molecules which make up liquid water, impurities such as gases and minerals also bond with the individual $H_2O$ molecules to fashion part of the tetrahedral arrays. However, the bonds formed between the $H_2O$ molecules, gases, and minerals throughout the arrays are the weak bonds developed from valance electron sharing. Thus, the operation of the nozzle arrangement disclosed in my U.S. Pat. No. 4,261,521, functions to break those weak bonds formed between the $H_2O$ molecules, gases, and minerals when the water is relatively quiescent.

My U.S. Pat. No. 4,261,521, discloses and describes a pair of vortex nozzles which are similar in construction and operate to impart a rotation to water passing through them. The nozzles are positioned in an opposed relationship so that the water streams exiting the nozzles rotate in opposite directions. The nozzles further function to expel the oppositely rotating water streams at a high velocity to collide the two streams at approximately halfway between the nozzle outlets. That collision between the counter-rotating streams creates compression waves throughout the water which coupled with the high velocity of the counter-rotating streams imparts a large amount of kinetic energy to the $H_2O$ molecules, gases, and minerals. In addition, the compression waves produce a shearing action which aids in tearing apart the molecular structure of the liquid water. Thus, the compression waves and resulting increase in kinetic energy facilitates the breaking of the bonds between the individual $H_2O$ molecules, the $H_2O$ molecules and the entrained gases, and the $H_2O$ molecules and the dissolved minerals.

Specifically, the compression waves alternately compress and expand the $H_2O$ molecules, entrained gases, and dissolved minerals, thereby, increasing their individual temperature. That increased temperature is reflected by increased electron energy and activity in the valence shells of the bonded $H_2O$ molecules, gases, and minerals. Because the added heat has no release into the atmosphere, the temperature of the $H_2O$ molecules, gases, and minerals continues to accumulate further increasing valence electron energy and activity. The accumulated heat/energy can only be dissipated through the release of the excited valence electrons. However, any release will break the bonds between the $H_2O$ molecules, gases, or minerals sharing those valence electrons, and further, will cause the breaking of some of the bonds formed between the hydrogen and oxygen atoms comprising the $H_2O$ molecules and the atoms comprising the gas molecules. Thus, at a point when sufficient heat has accumulated, valence electrons will be released to become free electrons, breaking the bonds formed between the $H_2O$ molecules, gases, and minerals. The initial breaking of a few bonds weakens other bonds which, aided by the shearing force of the compressional waves, facilitates the further release of valence electrons, thus, rending the arrays formed of tetrahedrons of bound $H_2O$ molecules and breaking the liquid water into its constituent parts (i.e. $H_2O$ molecules, hydrogen atoms, oxygen atoms, gas atoms, and minerals) and free electrons. The release of electrons is of extreme importance because it creates many ions, both positive and negative in the water.

The above constituent parts, upon exiting the vortex nozzle arrangement, begin to recombine, however, only individual $H_2O$ molecules and the individual tetrahedrons of $H_2O$ molecules reform because the increased energy imparted to the system has shattered the large arrays of bound tetrahedrons of $H_2O$ molecules, released entrained gases, and agglomerated minerals dissolved in the water. The $H_2O$ molecules remain free or aggregate into only the individual tetrahedrons because the bonds holding the large arrays together were shattered as described above and the water must remain quiescent for an extended time period (approximately 3-4 weeks) before the large arrays will reform.

Accordingly, the ability of the water to diffuse through permeable solids increases because the smaller sized individual $H_2O$ molecules and individual tetrahedrons of $H_2O$ molecules, when compared to the large arrays of bound $H_2O$ molecules, experience less resistance from permeable solids as they pass through them. In other words, the smaller size of the individual constituents comprising the water permits the water to more readily pass through permeable solids. Consequently, increased amounts of water flow through a permeable solid during a given time period. That increased rate of flow of the water through the permeable solid (i.e., the rate of diffusion) produces a corresponding increase in the pressure exerted against the permeable solid as the water flows through it (i.e., the osmotic pressure).

The entrained gases release to the atmosphere because the ionized gas atoms resulting from the collision of the water streams as described above combine with other atoms or ionized atoms and free electrons to form gas molecules. The formed gas molecules have increased energy and molecular movement which provide them with sufficient force to escape from the liquid water and return in their gaseous form to the atmosphere. The minerals agglomerate to appear in the liquid water as solids because the individual ionized elemental mineral atoms combine in sufficient numbers to form either a solid element or a solid compound depending upon the particular atoms involved. My U.S. Pat. No. 4,261,521, therefore, softens water by releasing entrained gases and agglomerating dissolved minerals. Additionally, my U.S. Pat. No. 4,261,521, increases the diffusion rate and, thus, the osmotic pressure (i.e., the pressure required to prevent diffusion during osmosis) by shattering the large arrays of bound $H_2O$ molecules so that free $H_2O$ molecules and individual tetrahedrons of $H_2O$ molecules remain.

An improvement over U.S. Pat. No. 4,261,521, is disclosed in my U.S. Pat. No. 5,318,702, which includes a pair of vortex nozzles of essentially identical design which impart a rotation in the same direction to water passing through them. The nozzles, however, are positioned in opposed relationship so that the direction of rotation of the water streams exiting the nozzles is opposite. The nozzles are each provided with at least one pair of slots which extend through the wall of the vortex nozzles. Each individual slot communicates with a chamber about the vortex nozzles which in turn communicates through a conduit with the exit stream of the nozzles. The addition of the slots to the nozzles enhances the performance of the nozzles disclosed in my U.S. Pat. No. 4,261,521. Namely, additional entrained gases are removed and mineral agglomerate size is significantly increased, while still providing an increased diffusion rate and, thus, osmotic pressure.

The slots operate to remove a fraction of the water from the rotating streams as they circulate about the nozzles prior to expulsion. The bled-off water, which is a product of interface chemistry, is then reintroduced via the chamber and conduit of each nozzle to the single water stream created beyond the impingement point of the two counter-rotating streams. In removing a small portion of the water from the two streams rotating about the vortex nozzles, the slots, essentially, bleed-off some $H_2O$ molecules as well as many of the free electrons and elemental ions created through the collision of the two counter-rotating streams. That occurs because the bond breaking process described above in reference to my U.S. Pat. No. 4,261,521, is not limited to the impingement point of the counter-rotating streams. The compressional waves which are largely responsible for the increased kinetic energy and shearing effect that destroy the bonds between the molecules and atoms continually travel throughout the two rotating streams. This means that the compressional waves break bonds at any location in the input water streams, thereby releasing free electrons and creating positive and negative ions throughout the entire input water streams.

The slots in removing $H_2O$ molecules, free electrons, and ions from the two rotating streams serve a twofold purpose. First, the extraction of $H_2O$ molecules, free electrons, and ions enhances the ability of the compressional waves to further separate the liquid water into its constituent parts because their removal weakens the remaining bonds. The remaining bonds are weakened because the removal of charge (i.e. free electrons and ions) from the rotating streams creates a charge void which allows the orbital distances between the bonded molecules, atoms, and valence electrons of the atoms to lengthen. Larger orbital distances mean that the cohesive forces keeping the molecules and atoms bonded together and the valence electrons orbiting about their atom's nucleus are greatly diminished. That translates into a lower energy threshold which must be overcome by the kinetic energy and shear forces of the compressional waves before bond breaking occurs. Thus, the weakening of the remaining bonds results in significantly larger numbers of broken bonds and attendant release of free electrons and creation of ions.

Second, the reintroduction of the $H_2O$ molecules, free electrons, and ions at a location beyond the counter-rotating streams' impingement point significantly increases the removal of entrained gases and agglomeration of the minerals. As previously described, the gas atoms and ions and free electrons combine with sufficient energy to escape the bonding forces of the liquid water and, therefore, return to the atmosphere. The mineral ions also combine to form elemental or compound solids. By introducing more ions and free electrons after most of the recombining has occurred, the above process which results in the escape of entrained gases and agglomeration of minerals continues even further.

For example, once several ions have formed a solid compound, the charge of that compound is balanced, or in other words canceled to zero. However, when free electrons or other ions are introduced, the electrically balanced compounds are prone to capture free electrons and once again become ionized. The re-ionized compound will seek an introduced oppositely charged ion or previously formed compound in an effort to balance its extra charge. Once an oppositely charged atom or compound is found, the two particles will bond, thereby, creating a solid compound larger than before. That bonding process will continue as long as additional free electrons and ions are introduced by the slots which means that repeated passes through the nozzles will improve the results. Thus, it should be apparent that rather large elemental or compound solids will be formed during the operation of the slotted nozzles. Such solids are easily removed by settling or filtration. The introduction of slots into the nozzle arrangement, therefore, greatly enhances the removal of entrained gases and significantly increases the ability of the minerals in solution to form solids and further agglomerate.

While both my U.S. Pat. No. 4,261,521, and my U.S. Pat. No. 5,318,702, are effective in removing entrained gases and minerals in suspension, it is desirable to produce nozzles which remove even more entrained gases from solution, increase mineral agglomeration to enhance their removal by filtration or settling, and produces a high degree of reduction in the size of molecular arrays found in liquids. My new invention provides a new nozzle design which accomplishes that. While the primary focus of my invention is in the treatment of water primarily for human consumption, it should be understood that other liquids may be treated in like manner for various purposes, many of which were discussed in my earlier patents.

SUMMARY OF THE INVENTION

The present invention deals primarily with the production of potable water using an apparatus for removing minerals such as calcium, iron, sulphur, and manganese and gases such as nitrogen and carbon dioxide. Additionally, the present invention provides a means for killing bacteria in the water. One of the reasons for the removal of certain minerals, specifically calcium, is to prevent its depositing on pipes, coffee pots, and other metal surfaces. It is also necessary to remove minerals of all types to soften the water for laundry purposes. In addition, and more importantly, minerals which produce unpleasant odors, taste, and color may be removed.

In accordance with the present invention, a vortex nozzle unit includes a cascaded vortex nozzle pair which includes a first vortex nozzle having a second vortex nozzle cascaded with it. The vortex nozzle unit further includes a second cascaded vortex nozzle pair which includes a third vortex nozzle having a fourth vortex nozzle cascaded with it. More particularly, the outlet from the second nozzle communicates with an inlet into the first nozzle and the outlet from the fourth nozzle communicates with an inlet into the second nozzle. Each of the four vortex nozzles receives water through an inlet which communicates with a water source to impart a rotation to the water passing through them.

The cascaded vortex nozzle pairs are positioned in opposed relation and communicate with a chamber so that the water streams exiting the first and third nozzles rotate in an opposite direction to collide at approximately the mid-point of the chamber. The two counter-rotating streams exiting the first and third nozzles collide at a high velocity to create a compression wave throughout the water. That compression wave imparts a large amount of kinetic energy to the $H_2O$ molecules and the gases and minerals trapped within the array of bound $H_2O$ molecules. Additionally, the compression waves produce a shearing action between the bonds among the $H_2O$ molecules, gases, and minerals which aids in tearing apart the molecular structure of the liquid water. Thus, the compression waves and resulting increase of kinetic energy facilitate the breaking of bonds between the individual $H_2O$ molecules, the $H_2O$ molecules and the entrained gases, and the $H_2O$ molecules and the dissolved minerals.

The second and fourth nozzles are cascaded with the first and third nozzles to introduce an additional water stream into their respective nozzle. The additional water streams enter the first and third nozzles to increase the velocity of the water within the first and third nozzles. That increase in velocity produces a corresponding increase in the strength of the compression waves produced by the first and third nozzles within the water. Furthermore, as the additional water streams from the second and fourth nozzles contact the water streams entering the first and third nozzles, respectively, they produce a shearing action between the streams which aids in the tearing apart of the molecular structure of the liquid water. Accordingly, the introduction of the additional streams and their corresponding collision with the water streams entering the first and third nozzles enhance the effects of the collision between the two counter-rotating streams in the chamber between the first and third nozzle.

In operation, the second and fourth nozzles introduce a rotating stream into the first and third nozzles, respectively, which combines with the stream rotating through those nozzles to increase the velocity of the streams exiting the first and third nozzles. That increased velocity results in an increased striking force between the collided streams which causes larger compression waves. Additionally, the rotating streams introduced into the first and third nozzles strike the streams entering those nozzles to produce compression waves which begins the breaking of bonds among the $H_2O$ molecules, gases, and minerals even before the streams exit the first and fourth nozzles to collide in the chamber. Those compression waves begun as a result of the collision between the water exiting the second and fourth nozzles and entering the first and third nozzles, respectively, combine with compression waves produced from the collision between the counter-rotating streams exiting the first and third nozzles. Consequently, the compression waves traversing the water streams within the cascaded nozzles has an increased amplitude which imparts larger amounts of kinetic energy to the $H_2O$ molecules, gases, and minerals, thereby increasing the shearing action against the molecular structure of the liquid water.

Furthermore, the streams of water entering the first and third nozzles from the second and fourth nozzles, respectively, contact the water entering the first and third nozzles at approximately a right angle to produce a shearing effect therebetween. That is, as the streams from the second and fourth nozzles and the first and third nozzles, respectively, contact at the entrance into the first and third nozzles, the shearing force of that collision breaks bonds between the $H_2O$ molecules, gases, and minerals due to their already weakened state as a result of the compression waves travelling through the water streams.

Thus, the increased velocity of the streams and the resulting increased amplitude compression waves along with the shearing action created at the mixing point between the pairs of cascaded vortex nozzles operate collectively to enhance the breaking of the molecular structure of the liquid water passed through the vortex nozzle unit. Each of the above functions to increase the temperature of the $H_2O$ molecules and the gases and minerals trapped in the array formed by the bound tetrahedrons of $H_2O$ molecules. That increase in heat/energy results in the release of valence electrons which breaks the bonds between the $H_2O$ molecules, gases, and/or minerals sharing those valence electrons. With the rending of those bonds, the array formed by the bound tetrahedrons of $H_2O$ molecules breaks into its constituent parts (i.e., $H_2O$ molecules, hydrogen atoms, oxygen atoms, gas atoms, and minerals) and free electrons. Furthermore, with the array of bound $H_2O$ molecules already weakened due to its rending by the compression waves, the shearing action of the streams entering the first and third nozzles from the second and fourth nozzles, respectively, breaks additional bonds to further reduce the liquid water into its constituent parts.

Accordingly, the nozzle unit of the present invention improves over my prior nozzle designs because its produces increased amplitude compression waves coupled with an additional shearing effect to provide a greater reduction of the array of bound H₂O molecules its constituent parts. Consequently, with more ions created in the water due to the release of more electrons, the cascaded nozzle design of the present invention disentrains more gases and agglomerates more of the minerals into larger sizes. More particularly, with increased amounts of ions and electrons, the ionized gases combine to form a gas which is released to the atmosphere and the ionized elemental mineral atoms combine to form a solid element or a solid compound which is of a size large enough for easy filtering or removal through settling.

Furthermore, with a greater rending of the array formed by bound tetrahedrons of $H_2O$ molecules due to the release of more electrons, the cascaded nozzle design of the present invention significantly increases the ability the treated water to diffuse through a permeable solid. That is, with a more effective shattering of the array formed by bound tetrahedrons of $H_2O$ molecules, increased amounts of free $H_2O$ molecules and individual tetrahedrons of $H_2O$ molecules are released from the array. As a result, the smaller sized individual $H_2O$ molecules and individual tetrahedrons of $H_2O$ molecules experience less resistance from the permeable solid as they pass through it. That is, the smaller size of the individual constituents comprising the water permits the water to more readily pass through the permeable solid. Consequently, increased amounts of water flow through a permeable solid during a given time period. That increased rate of flow of the water through the permeable solid (i.e., the rate of diffusion) produces a corresponding increase in the pressure exerted against the permeable solid as the water flows through it (i.e., the osmotic pressure).

Additionally, the cascaded vortex nozzles of the present invention destroy bacteria in the water. Specifically, as the compression waves traverse the water streams, they rapidly expand and contract the bacteria. That rapid expansion and contraction results in the rupturing of the cell structure of the bacteria, thereby destroying it. Thus, bacteria in water run through the cascaded nozzles of the present invention may be reduced and possibly even eliminated.

It is, therefore, an object of the present invention to provide a cascaded vortex nozzle design which disentrains gases and agglomerates solids in liquids.

It is another object of the present invention to provide a cascaded vortex nozzle design which increases the ability of liquids to diffuse through permeable solids and, thus, the osmotic pressure of the liquid.

It is a further object of the present invention to provide a cascaded vortex nozzle design which destroys bacteria in liquids.

Still other objects, features, and advantages of the present invention will become evident to those skilled in the art in light of the following.

DETAILED DESCRIPTION OF THE PREFERRED EMBODIMENT

Figure 1:
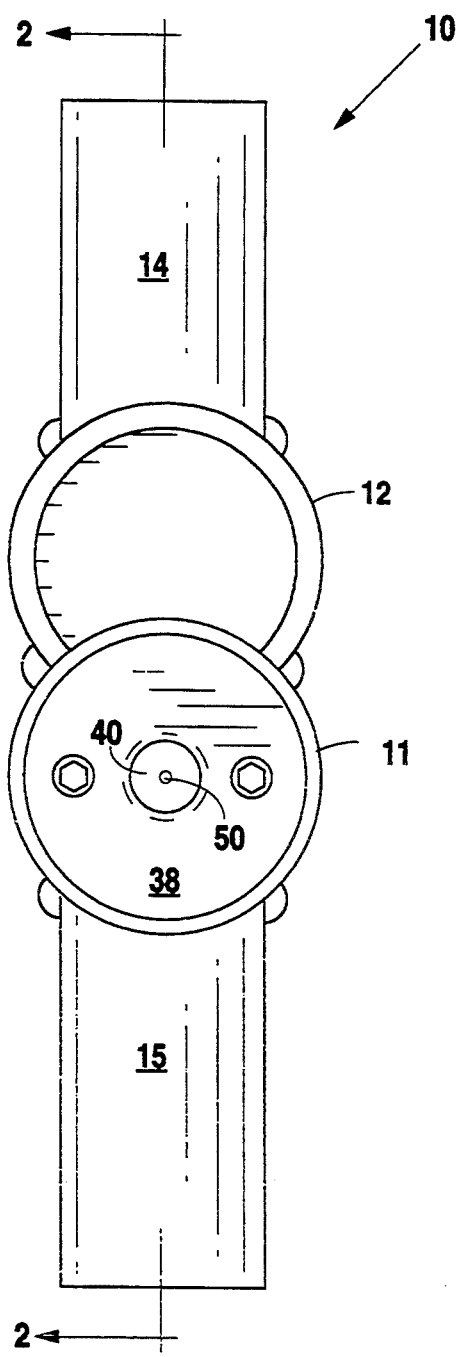
FIG. 1 is a side elevation view depicting the cascaded vortex nozzle unit of the present invention.
Figure 2:
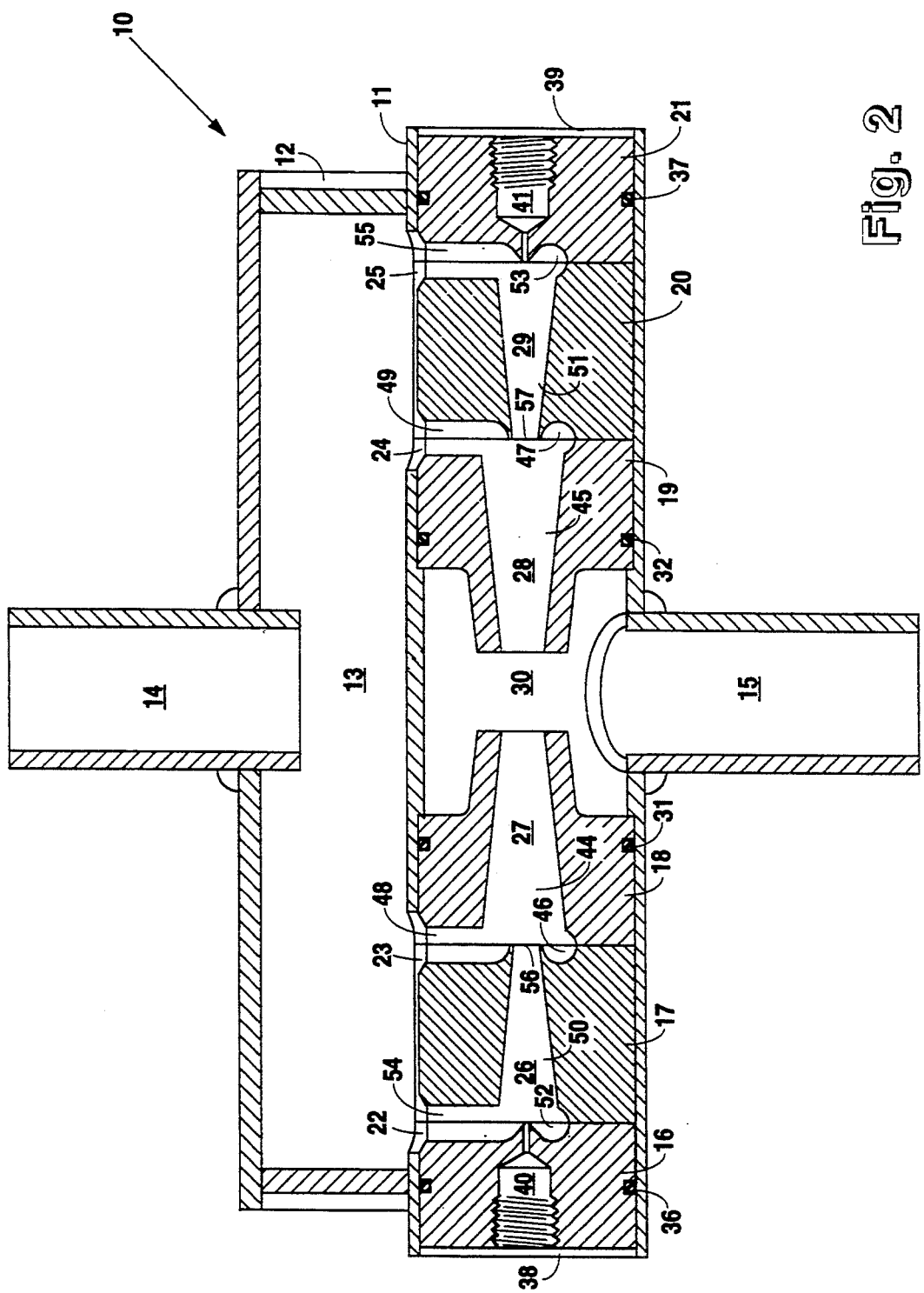
FIG. 2 is a front view taken in cross-section along lines 2, 2 of FIG. 1 depicting the cascaded vortex nozzle unit of the present invention.

As illustrated in FIGS. 1 and 2, cascaded vortex nozzle unit 10 includes cylindrical body portions 11 and 12 formed integrally using any standard machining or molding process. Cylindrical body portion 12 defines chamber 13 and includes inlet 14 which attaches to any suitable fluid source such as a well or public water source. Cylindrical body 11 defines a chamber and includes outlet 15 which attaches to any suitable reservoir or any suitable fluid delivery means such as a faucet, shower, or hose. While cascaded vortex nozzle unit 10 may be used to disentrain gases, agglomerate solids, and destroy bacteria in any fluid, for the purposes of disclosure, the fluid described will be water.

Cylindrical body portion 11 houses within its chamber vortex nozzle assembly blocks 16–21. Additionally, cylindrical body 11 includes inlets 22–25 which communicate with chamber 13 of cylindrical body portion 12. The structure of vortex nozzle assembly blocks 16–21 are similar to those described in my U.S. Pat. Nos. 4,261,521 and 4,957,626 and my allowed U.S. application Ser. No. 07/900,130, the disclosures of which are herein incorporated by reference. Each of vortex nozzle assembly blocks 16–21 are shaped to define a portion of vortex nozzles 26–29 using any standard machining or molding process.

Vortex nozzle assembly blocks 18 and 19 are inserted within the chamber defined by cylindrical body portion 11 until their inner edges contact protrusions 33–35. Protrusions 33–35 prevent vortex nozzle assembly blocks 18 and 19 from being inserted completely within the center of the chamber defined within cylindrical body portion 11. Vortex nozzle assembly blocks 18 and 19 reside within the chamber defined within cylindrical body portion 11 such that they define chamber 30 which communicates with outlet 15. Vortex nozzle assembly blocks 18 and 19 include o-rings 31 and 32, respectively, which form a fluid seal between vortex nozzle assembly blocks 18 and 19 and the inner surface of cylindrical body portion 11.

After the insertion of vortex nozzle assembly blocks 18 and 19 to the position shown in FIG. 2, vortex nozzle assembly blocks 17 and 20 are inserted until they abut the rear portions of vortex nozzle assembly blocks 18 and 19, respectively. Finally, vortex nozzle assembly blocks 16 and 21 are inserted until they abut the rear portions of vortex nozzle assembly blocks 17 and 20, respectively. Vortex nozzle assembly blocks 16 and 21 include 0rings 36 and 37, respectively, which form a fluid seal between vortex nozzle assembly blocks 16 and 21 and the inner surface of cylindrical body portion 11.

Cylindrical body portion 11 includes plates 38 and 39 which fit within the entrances at either end of cylindrical body portion 11. Plates 38 and 39 mount over vortex nozzle assembly blocks 16 and 21, respectively, using any suitable means such as screws to secure vortex nozzle assembly blocks 16–21 with the chamber defined by cylindrical body portion 11.

With vortex nozzle assembly blocks 16–21 positioned and secured within the chamber defined by cylindrical body portion 11, vortex nozzle assembly blocks 16–21 define vortex nozzles 26–29 and conduits 40 and 41. Vortex nozzles 27 and 28 are positioned in opposed relation so that a stream of water exiting their outlets 42 and 43, respectively, will collide approximately at the mid-point of chamber 30. Vortex nozzle assembly blocks 18 and 19 define frustro-conical inner surfaces 44 and 45 of vortex nozzles 27 and 28, respectively. The abutment of vortex nozzle assembly block 17 with vortex nozzle block 18 defines circular portion 46 and channel 48 which communicates with inlet 23. Additionally, outlet 56 from vortex nozzle 26 communicates with circular portion 46 of vortex nozzle 27. Similarly, vortex nozzle blocks 19 and 20 define circular portion 47 and channel 49 which communicates with inlet 24, while outlet 57 from vortex nozzle 29 communicates with circular portion 47 of vortex nozzle 28.

Vortex nozzle assembly block 17 defines frustro-conical inner surface 50, while the abutment between vortex nozzle assembly blocks 16 and 17 defines circular portion 52 and channel 54 which communicates with inlet 22. Vortex nozzle assembly block 20 defines frustro-conical inner surface 51 and the abutment between vortex nozzle assembly blocks 20 and 21 defines circular portion 53 and channel 55 which communicates with inlet 25. Vortex nozzle assembly blocks 16 and 21 include conduits 40 and 41, respectively, which communicate to the exterior of cylindrical body portion 11 via opening 56 in plate 38 (see FIG. 1) and another opening in plate 39 (not shown). Conduits 40 and 41 permit a bacteria killer such as chlorine to be introduced into vortex nozzles 26-29.

Thus, in operation, water is pumped into chamber 13 via inlet 14. The water flows from chamber 13 into each one of channels 54, 48, 49, and 55 via inlets 22-25, respectively, of cylindrical body portion 11. Channels 54, 48, 49, and 55 deliver the water to circular portions 52, 46, 47, and 53, respectively, of vortex nozzles 26-29. Circular portions 52, 46, 47, and 53 impart a circular rotation to the water and delivers the circularly rotating water streams into frustro-conical inner surfaces 50, 44, 45, and 51, respectively. Frustro-conical inner surfaces 50, 44, 45, and 51 maintain the circular rotation in their respective water stream and deliver the circularly rotating water streams to outlets 56, 42, 43, and 57, respectively, from vortex nozzles 26-29.

Due to the cascaded configuration of vortex nozzles 26 and 29, the water streams exiting their outlets 56 and 57 enter vortex nozzles 27 and 28, respectively. Those circularly rotating streams combine with the circularly rotating streams within vortex nozzles 27 and 28 to increase the velocity of the circularly rotating streams therein. Additionally, as the streams exiting vortex nozzles 26 and 29 contact the streams within vortex 27 and 28, they strike the circularly rotating streams within vortex nozzles 27 and 28 such that they create compression waves therein. Furthermore, the streams entering from vortex nozzles 26 and 29 shear the water entering vortex nozzles 27 and 28 from channels 48 and 49, respectively, to break bonds formed between the $H_2O$ molecules, the entrained gases, and dissolved solids.

The combined streams from vortex nozzles 26 and 27 and the combined streams from vortex nozzles 29 and 28 exit vortex nozzles 27 and 28 at outlets 42 and 43, respectively, and collide at approximately the mid-point of chamber 30. The streams rotating within vortex nozzles 27 and 28 travel in the same direction, however, the streams are rotating oppositely as they exit vortex nozzles 27 and 28 because vortex nozzles 27 and 28 are positioned in an opposed relationship. As the exiting streams collide, additional compression waves are created which combine with the earlier compression waves to create compression waves having amplitudes greater than the original waves. The compression waves destroy the large molecular arrays of the water as previously described to release free electrons and create ions within the combined water streams within chamber 30. The recombined water streams exit chamber 30 into inlet 15 where the ions and atoms recombine into gases that escape the water, solids that agglomerate for removal either through settling or filtration, and pure water without its original entrained gases. Furthermore, the $H_2O$ molecules recombine in smaller arrays or remain free which produces a water with an increased ability to diffuse through permeable solids. Consequently, the water's osmotic pressure increases because its increased ability to diffuse through permeable solids increases the pressure exerted against the permeable solids as the water flows through them. Additionally, the compression waves within the rotating streams destroy bacteria in the water by rupturing their cell structure as previously described.

Cascaded vortex nozzle unit 10 provides a significant commercial use in the field of desalination of salt water, particularly seawater. Presently, the various processes utilized to desalinate saltwater are extremely expensive due their relative ineffectiveness and the cost of the equipment involved. By passing saltwater through vortex nozzle unit 10, both equipment costs and their effectiveness in separating out the salt from the water may be significantly increased.

Specifically, after saltwater has been passed through vortex nozzle unit 10, its molecular structure which originally included $H_2O$ molecules bound together with salt, gases, and other minerals in large arrays will have been completely disrupted. As a result, gases escape while a portion of the salt and other minerals agglomerate, which allows their removal through filtration. Thus, the agglomeration of some of the salt lowers the concentration of salt in the remaining salt water.

Additionally, with the large arrays of molecules in the saltwater disrupted, its molecular structure breaks into the small tetrahedral arrays typically formed by $H_2O$ molecules and individual $H_2O$ molecules. Most of these tetrahedral arrays of $H_2O$ molecules and the individual $H_2O$ molecules will be bound to salt in solution, however, the complete disruption in the molecular structure of the saltwater will release some $H_2O$ molecules in their pure form. Consequently, similar to pure water, the treatment of the saltwater significantly enhances its ability to diffuse through permeable solids which, in turn, increases its osmotic pressure.

Typically, desalinating saltwater not passed through vortex nozzle unit 10 using reverse osmosis is virtually impossible because permeable solids that prevent the passage of the salt yet permit the passage of pure water are ineffective at the pressures required to force the large groups of tetrahedral arrays formed by the $H_2O$ molecules in the saltwater through them. However, saltwater passed through vortex nozzle unit 10 allows the use of reverse osmosis desalination techniques because the ability of the $H_2O$ molecules in the saltwater to diffuse through permeable solids has been significantly increased. That is, the small tetrahedral arrays of $H_2O$ molecules and individual $H_2O$ molecules produced in the saltwater experience considerably less resistance from permeable solids in passing through them. As a result, the pressure required during a reverse osmosis process to force the $H_2O$ molecules through permeable solids that prevent the passage of the salt yet permit the passage of the $H_2O$ molecules is lessened considerably which significantly increases the effectiveness of the permeable solids. Thus, a desalination process utilizing saltwater passed through vortex nozzle unit 10 is more effective in producing pure water and costs less than one using untreated saltwater.

Although the present invention has been described with a pair of cascaded nozzles in the foregoing embodiment, such description has been for exemplary purposes only, and, as will be apparent to those of ordinary skill in the art, any number of vortex nozzles may be cascaded to produce additional rupturing in the lattice structure of the fluid as well as destruction of bacteria. Furthermore, because many alternatives, equivalents, and variations of varying degrees will fall within the scope of the present invention, that scope, accordingly, is not to be limited in any respect by the foregoing description, rather, it is defined only by the claims which follow.

I claim:

1. An apparatus for increasing the diffusion rate of a fluid through permeable solids, releasing entrained gases from the fluid, agglomerating solids dissolved in the fluid, and destroying bacteria within the fluid, comprising:
   a first cascaded pair of vortex nozzles having inlets communicating with a fluid source and an outlet communicating a first rotating fluid stream to a fluid chamber;
   a second cascaded pair of vortex nozzles positioned in opposed relation to said first cascaded pair of vortex nozzles, said second cascaded pair of vortex nozzles having inlets communicating with said fluid source and an outlet communicating a second rotating stream to said fluid chamber to collide the second rotating fluid stream with said first rotating fluid stream in said fluid chamber.

2. The apparatus according to claim 1 wherein said first cascaded pair of vortex nozzles comprises a first vortex nozzle and a second vortex nozzle wherein an outlet from said second vortex nozzle communicates a rotating fluid stream into said first vortex nozzle to combine with a rotating fluid stream within said first vortex nozzle to form said first rotating fluid stream.

3. The apparatus according to claim 1 wherein said second cascaded pair of vortex nozzles comprises a first vortex nozzle and a second vortex nozzle wherein an outlet from said second vortex nozzle communicates a rotating fluid stream into said first vortex nozzle to combine with a rotating fluid stream within said first vortex nozzle to form said second rotating fluid stream.

4. The apparatus according to claim 1 further comprising means communicating with said first and second pair of vortex nozzles to deliver a bacteria killer into said first and second pair of vortex nozzles.

5. An apparatus for increasing the diffusion rate of a fluid through permeable solids, releasing entrained gases from the fluid, agglomerating solids dissolved in the fluid, and destroying bacteria within the fluid, comprising:
   a first vortex nozzle having an inlet communicating with a fluid source and an outlet communicating with a fluid chamber wherein said first vortex nozzle rotates a first fluid stream flowing through said first vortex nozzle;
   a second vortex nozzle cascaded with said first vortex nozzle, said second vortex nozzle having an inlet communicating with said fluid source and an outlet communicating with said first vortex nozzle wherein said second vortex nozzle rotates a second fluid stream flowing through said second vortex nozzle which enters said first vortex nozzle and combines with said first fluid stream;
   a third vortex nozzle having an inlet communicating with said fluid source and an outlet communicating with said fluid chamber wherein said third vortex nozzle rotates a third fluid stream flowing through said third vortex nozzle;
   a fourth vortex nozzle cascaded with said third vortex nozzle, said fourth vortex nozzle having an inlet communicating with said fluid source and an outlet communicating with said third vortex nozzle wherein said fourth vortex nozzle rotates a fourth fluid stream flowing through said fourth vortex nozzle which enters said third vortex nozzle and combines with said third fluid stream; and
   said first and third vortex nozzles positioned in opposed relation to collide the combined first and combined second fluid streams in said fluid chamber.

6. The apparatus according to claim 5 further comprising means communicating with said second and fourth vortex nozzles to deliver a bacteria killer into said second and fourth vortex nozzles.

* * * * *